US00PP23009P2

(12) United States Plant Patent
Bergman

(10) Patent No.: US PP23,009 P2
(45) Date of Patent: Sep. 4, 2012

(54) ***CHRYSANTHEMUM* PLANT NAMED 'CIDZ0009'**

(50) Latin Name: *Chrysanthemum×morifolium*
Varietal Denomination: CIDZ0009

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,622

(22) Filed: Aug. 5, 2011

(51) Int. Cl.
*A01H 5/00* (2006.01)

(52) U.S. Cl. ..... Plt./288

(58) Field of Classification Search ..... Plt./288
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0009' particularly distinguished by the large sized decorative inflorescences with pure white ray floret color, medium green foliage, strong and vigorous growth, excellent flowering uniformity, good branching and an 8.5 week flowering response.

1 Drawing Sheet

Latin name of the genus and species of the plant claimed: *Chrysanthemum×morifolium.*

Varietal denomination: 'CIDZ0009'.

BACKGROUND OF THE NEW PLANT

The present invention comprises a new *Chrysanthemum*, botanically known as *Chrysanthemum×morifolium*, and hereinafter referred to by the variety name 'CIDZ0009'.

'CIDZ0009' is a product of a planned breeding program. The new cultivar has large sized decorative inflorescences with pure white ray floret color, medium green foliage, strong and vigorous growth, excellent flowering uniformity, good branching and an 8.5 week flowering response.

'CIDZ0009' originated from a hybridization made in June 2006 in a controlled breeding environment in Salinas, Calif., USA. The female parent was the proprietary plant designated 'YB-A6182', unpatented, with white ray floret color, less vigor, one week faster flowering response, and spoon-type ray florets.

The male parent of 'CIDZ0009' was an unpatented, proprietary plant identified as 'YB-A8041' with cherry pink ray floret color and a more open-centered inflorescence. The resultant seed was sown in October 2006 in Fort Myers, Fla., USA.

'CIDZ0009' was selected as one flowering plant within the progeny of the stated cross in March 2007 in a controlled environment in Fort Myers, Fla., USA.

The first act of asexual reproduction of 'CIDZ0009' was accomplished when vegetative cuttings were propagated from the initial selection in June 2007 in a controlled environment in Fort Myers, Fla., USA.

BRIEF SUMMARY OF INVENTION

Horticultural examination of plants grown from cuttings of the plant initiated in June 2007, and continuing thereafter, has demonstrated that the combination of characteristics as herein disclosed for 'CIDZ0009' are firmly fixed and are retained through successive generations of asexual reproduction.

'CIDZ0009' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7067). 'CIDZ0009' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0009' with colors being as true as possible with an illustration of this type.

Figure 1:
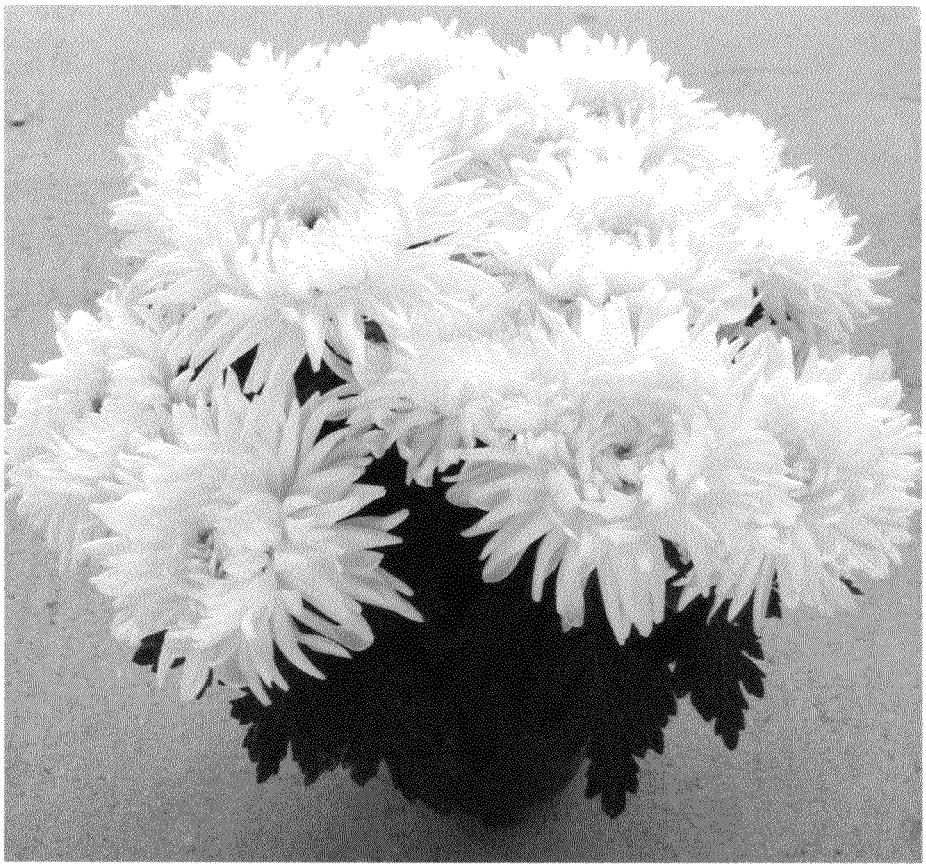
Figure 2:
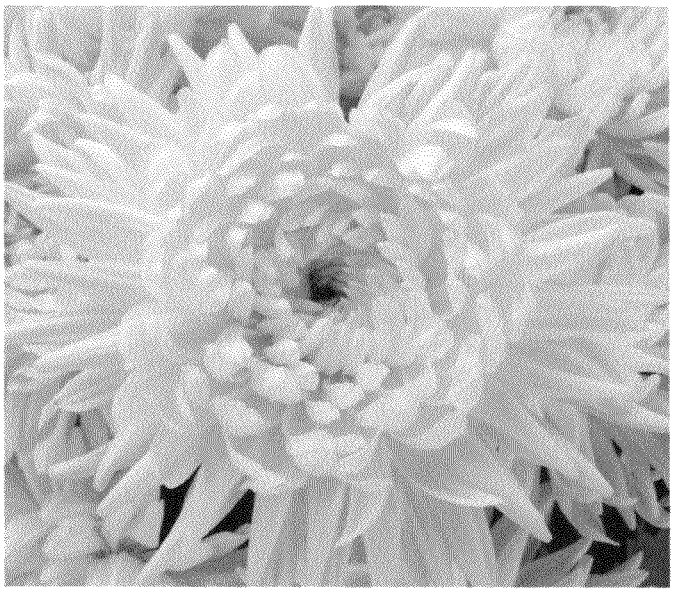

The photographic drawing shows in FIG. 1 four flowering potted plants of the new variety, and in FIG. 2 a close-up of the inflorescence.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a six inch pot, under greenhouse trial conditions Color references are made to The Royal Horticultural Society Colour Chart (R.H.S.) 2001.

TABLE 1

DIFFERENCES BETWEEN THE NEW VARIETY 'CIDZ0009' AND A SIMILAR VARIETY

| | 'CIDZ0009' | 'Yoolympia' (U.S. Plant Pat. No. 14,814) |
|---|---|---|
| Inflorescence diameter: | Larger | Smaller |
| Flowering response: | One week slower | One week faster |
| Quantity of ray florets: | Fewer | More |
| Quantity of disc florets: | More | Fewer |

Plant:
- *Form, growth and habit*.—Herbaceous pot-type, stems upright, freely branching, strong and vigorous growth habit.
- *Plant height*.—16-18.0 cm.
- *Plant height* (*inflorescence included*).—25-28.0 cm.
- *Plant width*.—18-20.0 cm.

Roots:
- *Number of days to initiate roots*.—About 4 days at about 22 degrees C.
- *Number of days to produce a rooted cutting*.—About 10 days at 22 degrees C.
- *Type*.—Fine, fibrous, free branching.
- *Color*.—RHS N155B but whiter.

Foliage:
- *Arrangement*.—Alternate, simple.
- *Immature, leaf color, upper surface*.—RHS 137A.
- *Lower surface*.—RHS 137C but greyer.
- *Mature, leaf color, upper surface*.—RHS 137A.
- *Lower surface*.—RHS 137C but greyer.
- *Length*.—6.7-7.5 cm.
- *Width*.—4.5-5.3 cm.
- *Shape*.—Ovate.
- *Base shape*.—Attenuate.
- *Apex shape*.—Mucronulate.
- *Margin*.—Entire; irregularly serrate.
- *Texture, upper surface*.—Bifid T-shaped hairs.
- *Lower surface*.—Bifid T-shaped hairs.
- *Color of veins, upper surface*.—RHS 138B.
- *Color of veins, lower surface*.—RHS 138B.
- *Petiole color*.—RHS 138B.
- *Length*.—1.5-2.0 cm.
- *Diameter*.—0.2-0.3 cm.
- *Texture*.—Bifid T-shaped hairs.

Stem:
- *Quantity of main branches per plant*.—3-5.
- *Color of stem*.—RHS 138A but appears lighter due to hairs.
- *Length of stem*.—20-24.0 cm.
- *Diameter*.—0.5-0.6 cm.
- *Length of internodes*.—1.0-2.0 cm.
- *Texture*.—Bifid T-shaped hairs.
- *Color of peduncle*.—RHS 138A but appears lighter due to hairs.
- *Length of peduncle*.—2.0 cm.
- *Peduncle diameter*.—0.3-0.4 cm.
- *Texture*.—Bifid T-shaped hairs.

Inflorescence:
- *Type*.—Compositae type, solitary decorative-type inflorescences borne terminally above foliage, ray florets arranged acropetally on a capitulum.
- *Quantity of short days to flowering* (*response time*).—About 8.5 weeks.
- *Quantity of inflorescences per plant*.—3-5.
- *Lastingness of individual blooms on the plant*.—About 4 weeks.
- *Fragrance*.—Slightly spicy.

Bud (just before opening/showing color):
- *Color*.—None on the plant to observe.

Immature inflorescence:
- *Diameter*.—7.0-8.0 cm.
- *Color of ray florets, upper surface*.—RHS N155B but whiter.
- *Lower surface*.—RHS N155B but whiter.

Mature inflorescence:
- *Diameter*.—13-14.0 cm.
- *Depth*.—3.5-4.2 cm.
- *Total diameter of 'disc'*.—Visually indistinct.
- *Receptacle height*.—0.7-0.8 cm.
- *Receptacle diameter*.—1.2 cm.

Ray florets:
- *Average quantity of florets*.—Approximately 110 in numerous whorls.
- *Color of florets, upper surface*.—RHS N155B but whiter.
- *Lower surface*.—RHS N155B but whiter.
- *Length*.—4.1-6.5 cm.
- *Width*.—0.9-1.0 cm.
- *Shape*.—Elliptical; but some are semi-spoon at the immature stage.
- *Apex shape*.—Irregular and slightly emarginate.
- *Margin*.—Entire.
- *Texture, upper surface*.—Papillose.
- *Lower surface*.—Papillose.

Disc florets:
- *Average quantity of florets*.—Approximately 35.
- *Color of florets*.—RHS 1C with RHS 7B apex.
- *Length*.—0.6 cm.
- *Width*.—0.1 cm.
- *Shape*.—Tubular, elongated.
- *Apex shape*.—Acute, 5 pointed.

Phyllaries:
- *Quantity*.—Approximately 30.
- *Color, upper surface*.—RHS 137B.
- *Lower surface*.—RHS 137A but appears lighter due to hairs.
- *Length*.—1.2 cm.
- *Width*.—0.3-0.4 cm.
- *Shape*.—Lanceolate.
- *Apex shape*.—Acute.
- *Base*.—Fused.
- *Margins*.—Entire; papery.
- *Texture, upper surface*.—Glabrous.
- *Lower surface*.—Bifid T-shaped hairs.

Reproductive organs:
- *Pistil*.—1.
- *Found on both florets*.—Yes.
- *Length*.—0.6-0.7 cm.
- *Style color*.—RHS 1C but more green.
- *Style length*.—0.5-0.6 cm.
- *Stigma color*.—RHS 7A.
- *Stigma shape*.—Bi-parted.
- *Ovary color*.—Not observed.
- *Stamens*.—4.
- *Found on only disc florets*.—Yes.
- *Color of filaments*.—RHS 1C.
- *Length filaments*.—0.2 cm.
- *Anther color*.—RHS 9A.
- *Anther length*.—0.1 cm.

*Anther shape*.—Oblong.

*Color of pollen*.—Not observed.

*Pollen amount*.—Not observed.

*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0009' substantially as illustrated and described herein.

* * * * *